(12) United States Patent
Lindhofer et al.

(10) Patent No.: US 6,994,853 B1
(45) Date of Patent: Feb. 7, 2006

(54) TIME-STAGGERED UTILIZATION OF TUMOR CELLS IN COMBINATION WITH INTACT ANTIBODIES FOR IMMUNIZATION

(75) Inventors: Horst Lindhofer, Groebenzell (DE); Peter Ruf, Schoengeising (DE)

(73) Assignee: Trion Pharma GmbH, München (DE)

( * ) Notice: Subject to any disclaimer, the term of this patent is extended or adjusted under 35 U.S.C. 154(b) by 0 days.

(21) Appl. No.: 09/787,970

(22) PCT Filed: Sep. 22, 1999

(86) PCT No.: PCT/EP99/07094

§ 371 (c)(1),
(2), (4) Date: Sep. 26, 2001

(87) PCT Pub. No.: WO00/18435

PCT Pub. Date: Apr. 6, 2000

(30) Foreign Application Priority Data

Sep. 25, 1998 (DE) .................................. 198 44 157
Dec. 21, 1998 (DE) .................................. 198 59 115

(51) Int. Cl.
*A61K 39/395* (2006.01)
*C07K 16/28* (2006.01)
*C07K 16/30* (2006.01)

(52) U.S. Cl. ............................ 424/136.1; 424/130.1; 424/138.1; 424/154.1; 424/155.1; 424/156.1; 424/277.1; 424/93.7; 530/387.3; 530/388.85

(58) Field of Classification Search ............ 424/130.1, 424/136.1, 156.1, 138.1, 154.1, 155.1, 277.1, 424/93.7; 530/387.3, 388.85

See application file for complete search history.

(56) References Cited

U.S. PATENT DOCUMENTS

| | | | |
|---|---|---|---|
| 5,837,248 A * | 11/1998 | Kikuchi et al. | |
| 5,985,276 A | 11/1999 | Lindhofer et al. | |
| 6,235,785 B1 * | 5/2001 | Jedlitschky et al. | ........ 514/568 |
| 6,458,369 B1 * | 10/2002 | Berd | ........ 424/277.1 |
| 6,551,592 B2 * | 4/2003 | Lindhofer et al. | ........ 424/136.1 |

FOREIGN PATENT DOCUMENTS

| | | |
|---|---|---|
| DE | 19710497 C2 | 3/1998 |
| EP | 0885614 B1 | 12/1998 |

OTHER PUBLICATIONS

Lindhofer et al, Annual meeting international society for experimental hematology XX, XX, 1997, 25:879, abstract 527.*
Multihoff et al (Int. J. Cancer 61:272-279, 1995).*
Campbell et al., "The role of tumor rejection antigens in host antitumor defense mechanisms," *Cancer* (1995) 75(11): 2649-55.
Lindhofer et al., "Bispecific antibodies target operationally tumor-specific antigens in two leukemia relapse models," *Blood* 1996) 88(2): 4651-58.
Lindhofer et al., "Bispecific antibodies effectively purge cancer cells from peripheral blood stem cell collections without affecting colony forming units," Annual Meeting International Society for Experimental Hematology, XX, XX (1997) 25(8): 879.

* cited by examiner

*Primary Examiner*—Alana M. Harris
*Assistant Examiner*—Anne L. Holleran
(74) *Attorney, Agent, or Firm*—Townsend and Townsend and Crew LLP

(57) ABSTRACT

The invention relates to the time-staggered utilization of tumor cells in combination with intact, preferably heterologous antibodies for the immunization of humans and animals.

39 Claims, 8 Drawing Sheets

Figure 4:
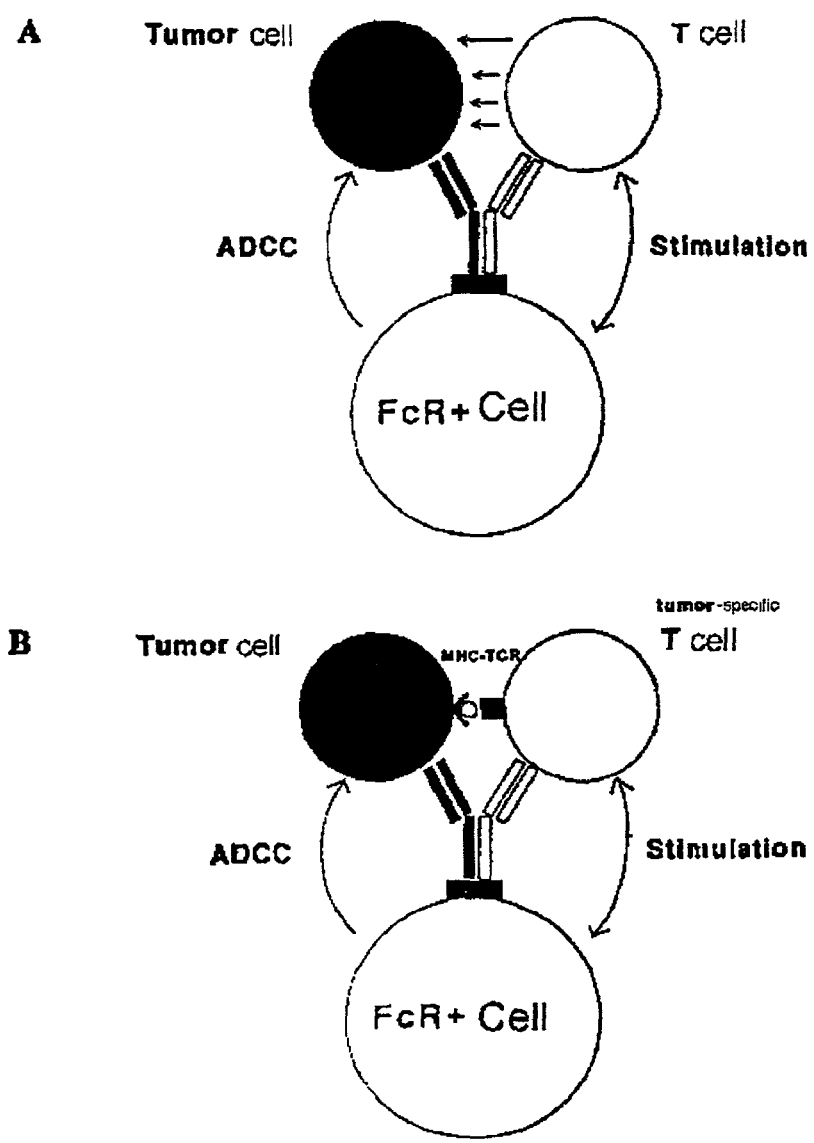

Fig. 1
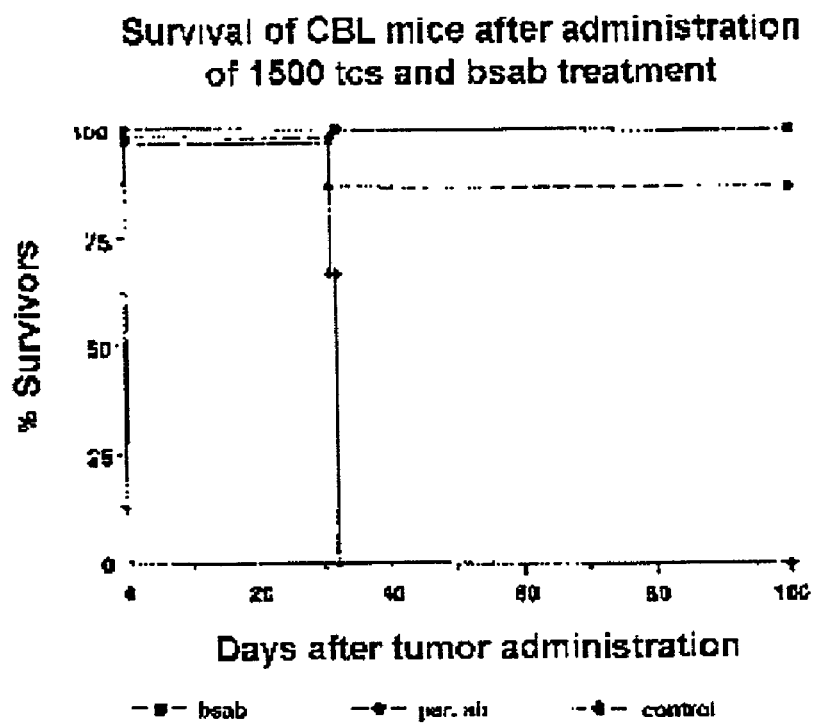
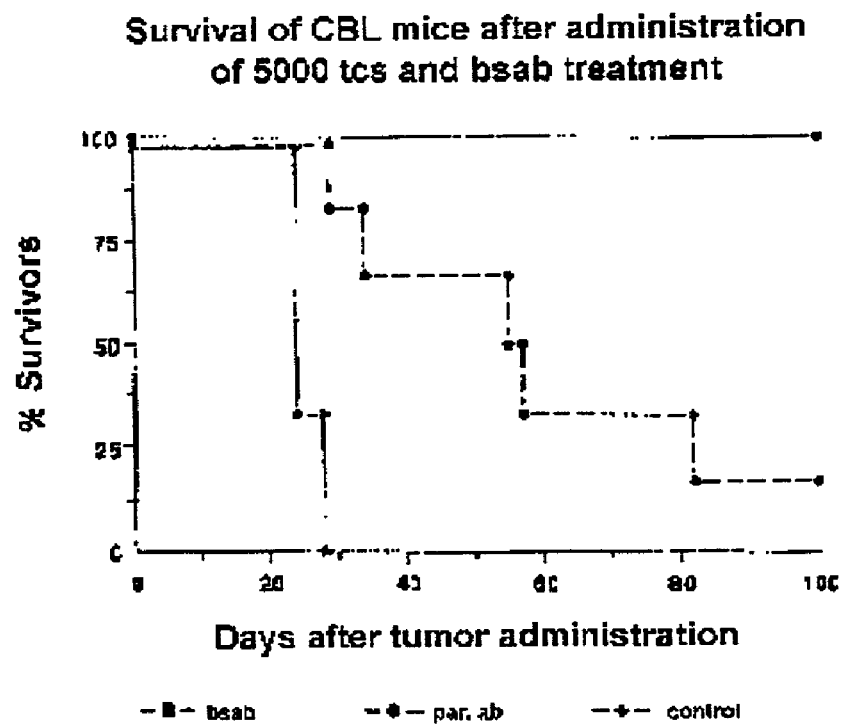

Fig. 2
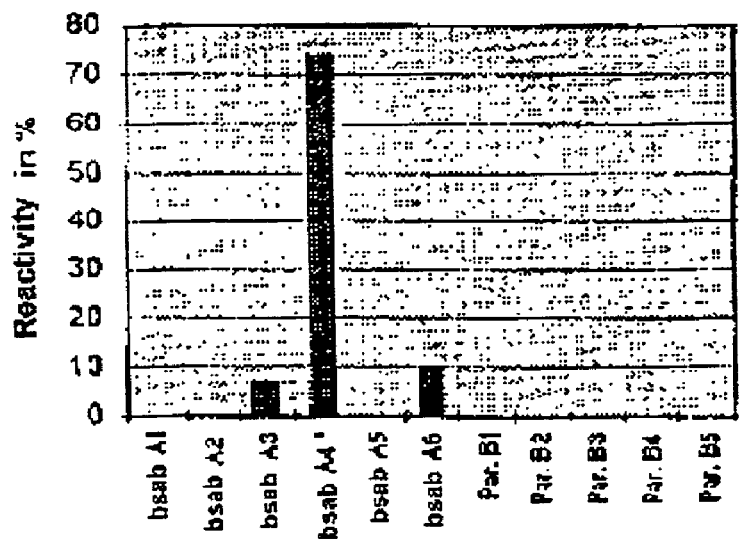
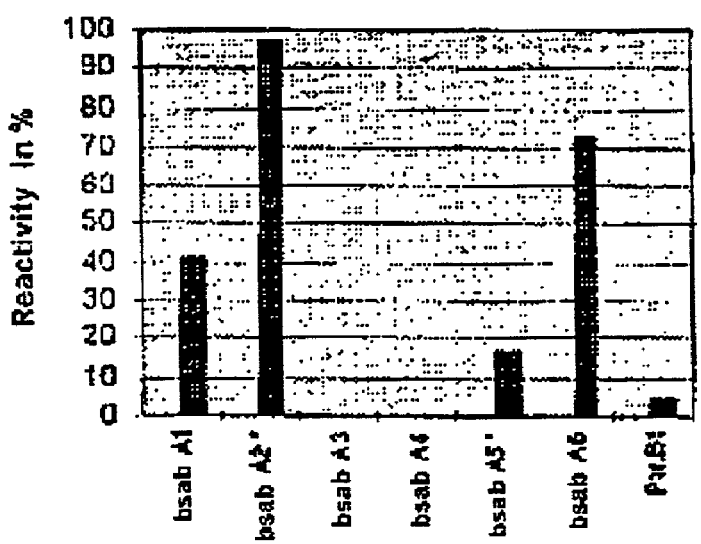

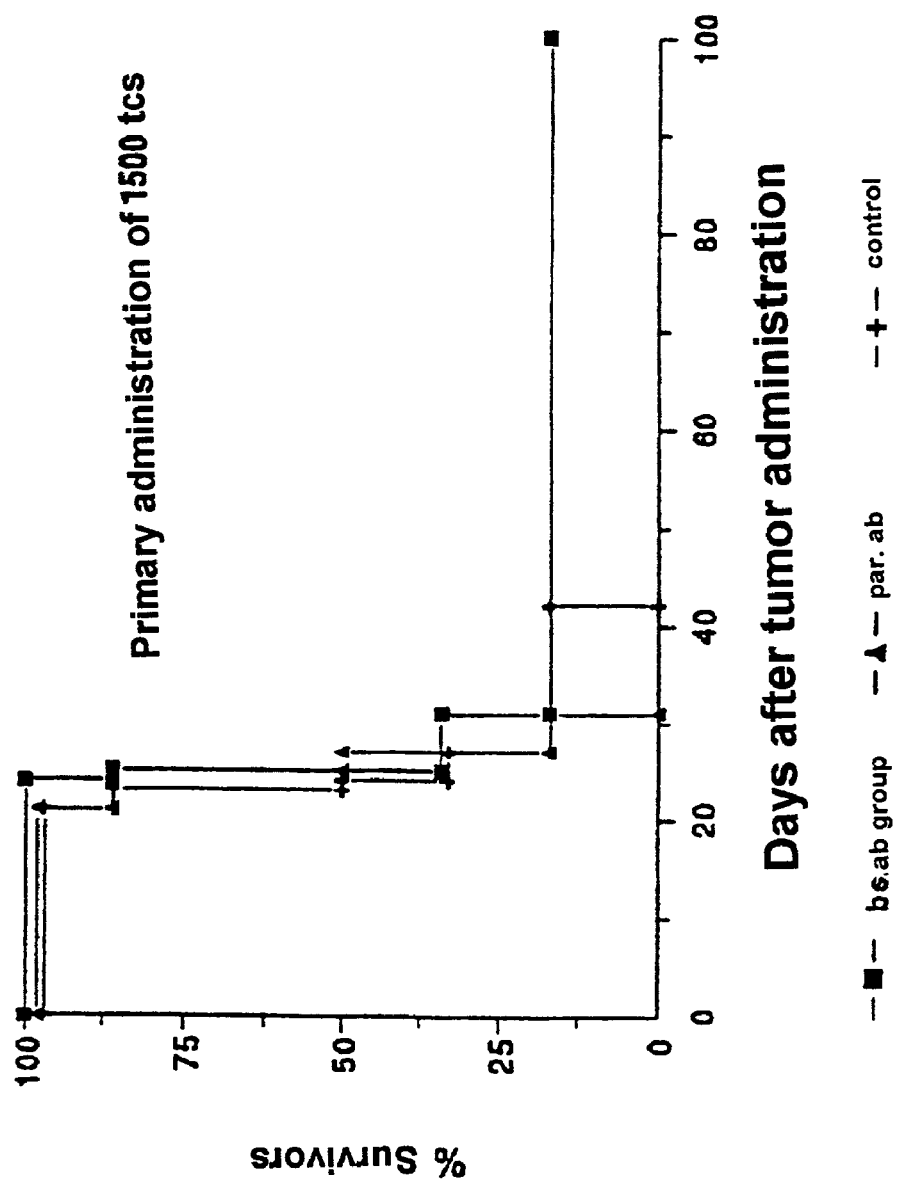

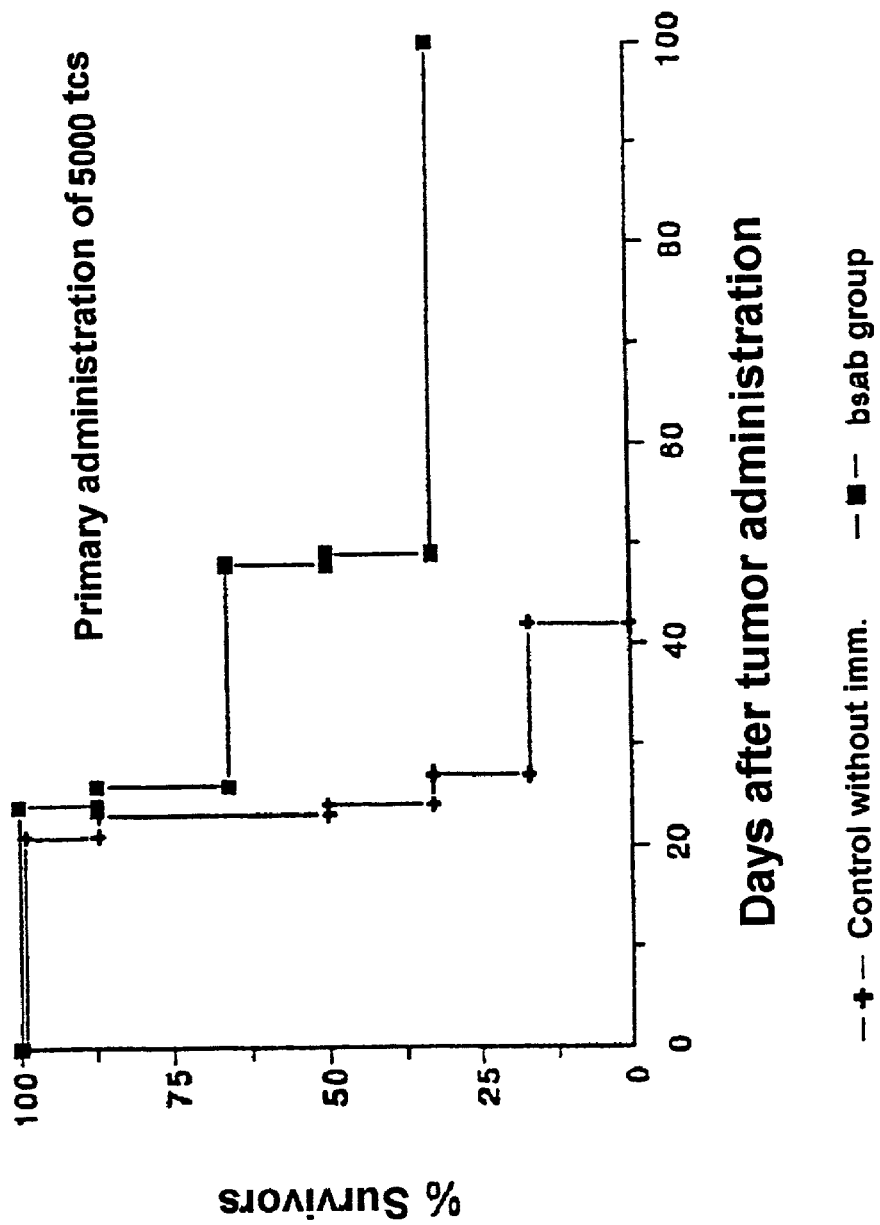

Role of accessory cells in the tumor immunotherapy using bispecific antibodies

Fig. 7 A + B
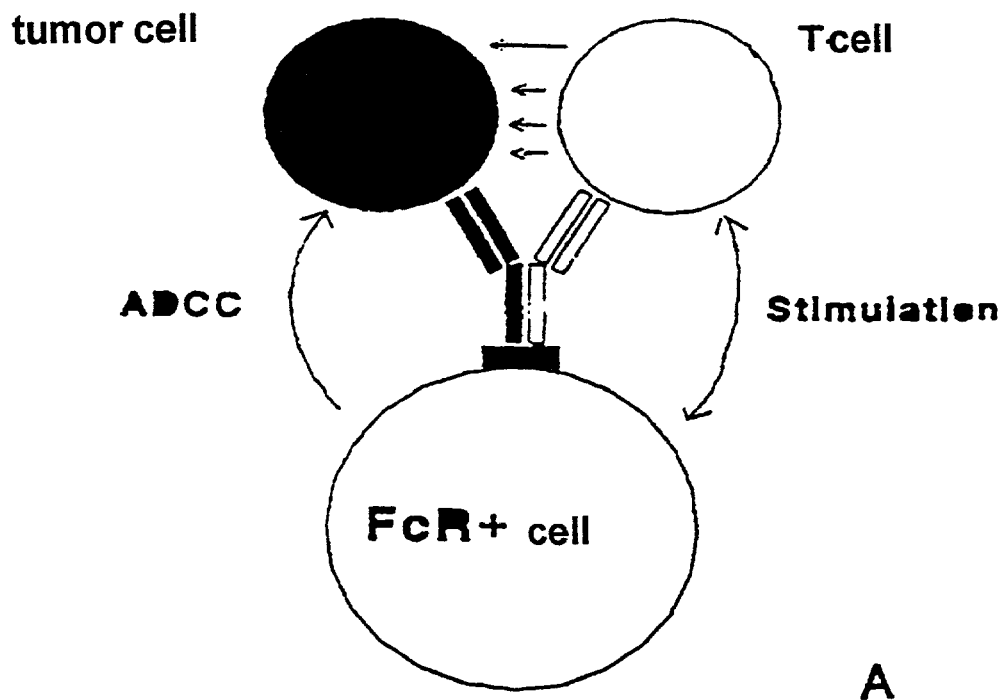
A
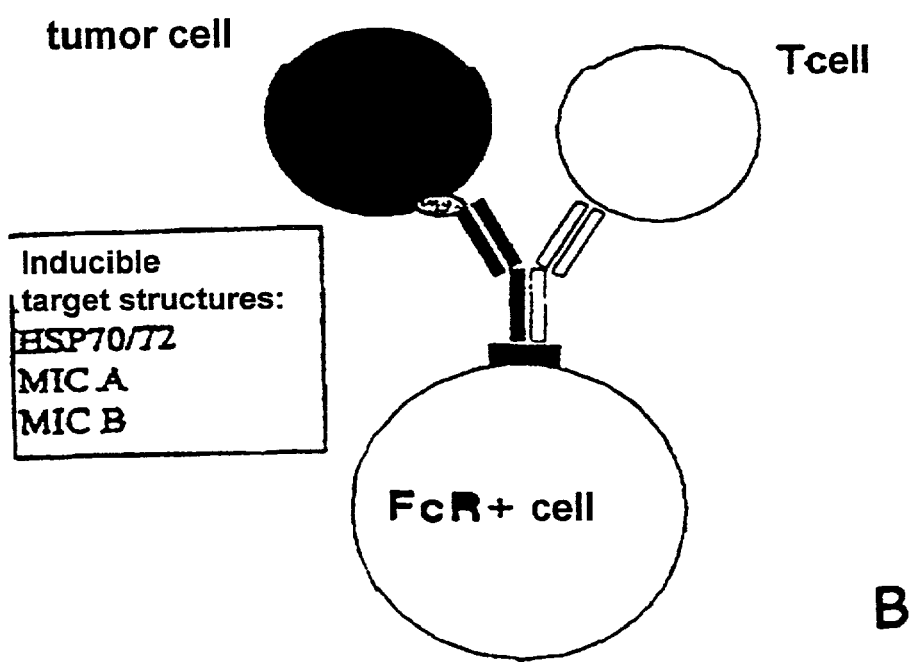
B

TIME-STAGGERED UTILIZATION OF TUMOR CELLS IN COMBINATION WITH INTACT ANTIBODIES FOR IMMUNIZATION

This application is the national stage under 35 U.S.C. §371 of PCT/EP99/07074, filed Sep. 22, 1999.

The invention relates to the time-staggered utilization of tumor cells in combination with intact, preferably heterologous antibodies for immunization of humans and animals.

In recent years, immunotherapy using antibodies, especially bispecific or trispecific antibodies, has gained increasing importance. However, a substantial problem in the use of such antibodies in immunotherapy is for example the activation of cells of the immune system, e.g. of T lymphocytes.

DE 196 49 223 and DE 197 10 495 describe intact bispecific and trispecific antibodies which are employed in immunotherapy. These bispecific and trispecific antibodies are capable of binding to a T cell, at least an antigen on a target cell and, by their Fc portion or by a third specificity, to Fc receptor-positive cells (accessory cells).

It is an object of the present invention to provide a novel use for a combinatory preparation containing tumor cells treated in a way to prevent their survival after reinfusion as well as intact bispecific and/or trispecific antibodies directed against the tumor cells.

According to the present invention, this object has been achieved by administrating to the human or animal to be immunized autologous tumor cells or allogenic tumor cells of the same type of tumor each of which have been treated to prevent their survival following reinfusion in a time-staggered fashion in combination with intact bispecific and/or trispecific antibodies having the following properties of:

(α) binding to a T cell;
(β) binding to at least one antigen on a tumor cell;
(γ) binding, by their Fc portion (in the case of bispecific antibodies) or a third specificity (in the case of trispecific antibodies), to Fc receptor-positive cells.

According to the present invention, the tumor cells and antibodies form a functional entity and are administered in the form of a combination to achieve an immunization in a targeted way wherein it is essential for a successful utilization that the application is performed in a time-staggered manner. Principally, it is possible to first administer the treated tumor cells followed, in a time-staggered manner, by the antibodies, or to administer to the patient first the antibodies followed, in a time-staggered manner, by the tumor cells.

Preferably, the interval between administration of the tumor cells and the antibodies or vice versa is about 1–48 hours. Particularly preferred is an interval of 1–24 hours, further preferred 1–12 hours. Furthermore, intervals of 1–6 hours or 2–4 hours are possible. For the success of the present invention it is important that the application is carried out in a time-staggered manner wherein the interval to be used may also depend on the type of tumor to be treated and the antibody used. The optimal interval in each case may be determined by the skilled artisan by means of experimentation.

The tumor cells employed should be administered intact if possible. However, it is necessary to prevent their survival after reinfusion. For this purpose it has been found reasonable to either subject the tumor cells to irradiation or to prevent their survival after reinfusion by chemical agents. By these two types of treatment particularly the outer structure of the tumor cells remains unchanged, i.e. the pattern recognized by antibodies.

Preferably, gamma-irradiation is used for irradiation, preferably at a dose of 20–200 Gy. For a chemical treatment, mitomycin C has been particularly successful. It is especially preferred to use heterologous bispecific and/or trispecific antibodies.

The success of the immunization may be further improved by administering the antibodies and the tumor cells several times, each in a time-staggered fashion. A further improvement of the immunogenicity of the tumor cells may be achieved by subjecting them to a heat pretreatment prior to infusion. The preferred range is 41–42° C. where the optimal temperature may be determined by experimentation. Preferred results are achieved at a temperature of about 41.8° C. The time of the heat pretreatment generally is 1 to 6 hours, preferably 3 hours. The time as well as the temperature which may be optimally employed depend on the type of tumor to be treated. The respective optimal values may be determined by the skilled artisan performing laboratory experimentation.

As could be demonstrated in the syngeneic (autologous) murine tumor model also other factors play an important role for a particularly successful induction of the immunity. Thus, the spatially correct delivery of the tumor material is of importance. It is necessary to deliver the tumor cells to the immune cells responsible for immunization in the correct spatial context. In this respect, an intravenous (i.v.), intraperitoneal (i.p.), or subcutaneous (s.c.) application has proven to be especially favorable, because thereby by using the bispecific and/or trispecific antibodies an optimal contact in these compartments with the corresponding immune cells is ensured.

For a successful immunization it is further advantageous that the amount of tumor cells administered is selected in an appropriate manner. Thus, in experiments using the murine tumor model it has been demonstrated that the desired successful immunization is not achieved if the number of tumor cells is too low. In contrast, if the amount of tumor cells is too high it may have an adverse effect for example because of the occurrence of tolerance phenomena. If these results are transferred to the situation in the patient, this means that it may be advantageous for the success of the immunization to administer a defined amount of tumor material in the correct spatial context together with an equally defined amount of antibodies. Although a successful immunization can be achieved without having optimized one of these parameters, particularly good results are achieved if both the amounts of the antibodies and the amount of tumor material as well as the spatial context have been adjusted to each other and have been optimized.

Considering the above discussion, for example an insufficient immune protection may be established if the number of tumor cells is too low. Therefore, it is necessary for complete success of the immunization that the immunization is performed with a defined number of activated tumor cells and a defined amount of bispecific and/or trispecific antibodies. The respective values may be determined by the skilled artisan by means of experimentation.

The bispecific and/or trispecific antibodies employed according to the present invention are preferably administered in an amount of 5–500 µg, further preferred 10–300 µg, 10–100 µg or 10–50 µg, each per infusion. The amount of antibody employed depends on the type of tumor to be treated, the response of the patient and other factors. The optimal amounts may be determined by the skilled artisan by means of experimentation.

Preferably, the tumor cells are administered in an amount of $10^7$–$10^9$ cells per infusion, while a cell number of about $10^8$ has proven to be preferred. As detailed above, the tumor cells have been treated prior to reinfusion in a way to prevent their survival after reinfusion wherein optionally they may be subjected to an additional heat pretreatment. For details see the present specification.

However, it is indispensable to administer the tumor cells and the antibodies in a time-staggered manner. This serves to ensure that by injection of the bispecific and/or trispecific, preferably heterologous antibody into the animals or humans to be treated, because of an excess of T lymphocytes present in peripheral blood these will be bound and preactivated via the high-affinity binding arm. In addition, also Fc receptor-positive accessory immune cells present may be bound via the Fc portion of the bispecific or trispecific antibody. If this cellular complex of the T cell and the Fc receptor-positive cell is then directed via the second high-affinity tumor binding arm to the tumor cells which are present in a relatively low number, these will be destroyed by T lymphocytes or Fc receptor-positive cells, respectively, and phagocytozed by Fc receptor-positive cells integrated in the cellular complex, such as macrophages. This has already been demonstrated experimentally using labeled human monocytes/macrophages and tumor cells. In a next step, the tumor material incorporated will be processed and presented to the immune system via MHC class I and particularly class II molecules which is an important prerequisite for the humoral immune reaction observed.

As demonstrated by the Example according to the present invention, the detection of tumor-reactive antibodies formed after a therapy is dependent on the activation of CD4+ tumor-specific T lymphocytes which are capable of stimulating tumor-specific B cell clones by means of T/B cell cooperation. Thus, by the detection of a humoral immune reaction indirectly there could also be provided evidence for a cellular CD4 T cell response and thereby an explanation for the survival of the mice as a result of the time-staggered administration of tumor cells and antibodies was provided.

EXAMPLE 1

The development of a long-lasting immune protection against the tumor by means of bsabs was examined in a murine autologous tumor model. First, C57Beispiel/6 mice received a principally lethal dose of autologous melanoma cells and, after two days, a second injection of parental or bispecific antibodies, respectively. To test for the development of a long-lasting immune protection in the mice the surviving mice were subjected to another tumor administration after 100 days, in this case, however, without ab. Furthermore, to address the question in how far the number of tumor cells administered plays a role for development of an immune protection, the experiments were performed using a low tumor dose of 1500 tumor cells (tcs) as well as a high tumor dose of 5000 tumor cells. Moreover, besides survival of the mice also the presence of a humoral immune response against the tumor was used as another criterion for the presence of an immune protection. For this purpose, sera of the mice prior to as well as 100 days following the treatment (i.e. immediately prior to the second tumor administration) were compared with respect to the presence of anti-tumor antibodies.

FIG. 1 shows the survival curves of the mice after the primary tumor administration with 1500 or 5000 tumor cells, respectively. While all of the control mice without antibody treatment died within 35 days, all of the bsab-treated mice could be cured. In comparison, of the mice treated with a combination of the two parental abs only 84% survived after the low tumor dose and only 16% survived after the high tumor dose.

This qualitative difference between bsabs and parental abs was also observed with respect to the development of a humoral immune reaction. FIG. 2 shows the humoral immune response against the tumor cells as measured by flow cytometry. While the survivors of the "parental group" showed no humoral immune response, this was observed in the mice of the "bispecific group". Particularly important in this respect, however, was the amount of tumor material administered. There was a significant difference between the groups having a low or a high amount of tumor administered. After a low tumor dose given only 17% of the mice had a strong and 33% a weak titer while a strong titer could be detected in 66% of the mice with the higher tumor dose.

Furthermore, the data obtained with respect to humoral immune reaction obviously correlate with the survival of the mice following the second tumor administration but without subsequent antibody injection. Only mice having developed a strong antibody titer against the tumor survived the tumor administration or died with a long delay as compared to the control group without immunization. In contrast, all mice without detectable titer died first and without delay as compared to the control. FIG. 3 shows the survival curves of the mice having received a second tumor administration without having been subjected to another antibody treatment afterwards. Mice having received a high primary dose of 5000 tcs showed a markedly better survival rate compared to the mice with a low-dose primary tumor administration of 1500 tcs.

The antibodies useful according to the present invention are capable of activating the Fc receptor-positive cell whereby the expression of cytokines and/or co-stimulatory antigens is initiated or increased.

In the case of the trispecific antibodies, binding to the Fc receptor-positive cells preferably occurs for example via the Fc receptor of Fc receptor-positive cells or alternatively via other antigens on Fc receptor-positive cells (antigen-presenting cells) such as the mannose receptor.

By means of the time-staggered application of intact, preferably heterologous bispecific and/or trispecific antibodies of the present invention, an anti-tumor immunity and preferably a long-lasting anti-tumor immunity is developed in the patient. The administration (reinfusion) is performed preferably in a patient following the treatment of the primary tumor, preferably in patients in a minimal residual disease (MRD) situation. In patients with a low amount of residual tumor cells in which however the risk of recidivation may be high, the time-staggered application described according to the present invention is especially successful.

The heterologous bispecific and/or trispecific antibodies which may be used according to the present invention partly are known per se but partly are described for the first time in the above application. An example for a bsab is antibody anti-CD3 x anti-EpCAM (GA-733-2) which is employed in epithelial tumors such as the mammary carcinoma.

On the tumor cell, an up-regulation of MHC I as well as an activation of the intracellular processing machinery (proteasome complex) occurs due to the release of cytokins (such as INF-$\gamma$ and TNF-$\alpha$) in the vicinity of the tumor cell. The cytokines are released due to the bispecific antibody-mediated activation of T cells and accessory cells. This means that by the intact bsab not only tumor cells are destroyed or phagocytozed but indirectly also the anti-tumor immunogenicity is increased.

Activation of the Fc receptor-positive cell by the bsab is dependent on the subclass or the subclass combination, respectively. As demonstrated by in vitro experiments, for example, bsabs of the mouse-IgG2a/rat-IgG2b subclass combination are able to bind to and simultaneously activate Fc receptor-positive cells leading to an up-regulation or new formation (expression), respectively, of co-stimulatory antigens such as CD40, CD80, or CD86 on the surface of these cells, while bsabs of the mouse-IgG1/rat-IgG2b subclass combination are able to bind to Fc receptor-positive cells ((1) Haagen et al., J. Immunology, 1995, 154: 1852–1860) but obviously are unable to activate these cells to a comparable extent ((2) Gast et al., Cancer Immunol. Immunother., 1995, 40: 390).

While the intact bsab simultaneously binds to and activates the T cell with one binding arm (e.g. CD3 or CD2), co-stimulatory signals from the Fc receptor-positive cell bound to the Fc portion of the bsab may be transferred to the T cell. I.e., only the combination of T cell activation via one binding arm of the bsab and simultaneous transfer of co-stimulatory signals from the Fc receptor-positive cell to the T cell leads to an efficient T cell activation (FIG. 4A). Also, tumor-specific T cells which have been insufficiently activated at the tumor cell and are therefore anergic may be reactivated by the ex-vivo pretreatment of the present invention (FIG. 4B).

Another important aspect in the induction of an anti-tumor immunity is the possible phagocytosis, processing and presentation of tumor components by the accessory cells (monocytes/macrophages, or dendritic cells) which have been targeted by the bsab. By this classical mechanism of antigen presentation both tumor-specific CD4- as well as CD8-positive cells may be generated. Moreover, tumor-specific CD4 cells play an important role in the induction of a humoral immune response in the context of T/B cell cooperation.

Bispecific and trispecific antibodies are able to bind to the T cell receptor complex of the T cell with one binding arm and to tumor-associated antigens on the tumor cell with the second binding arm. Thereby, they activate T cells which destroy the tumor cells by releasing cytokines or by apoptosis-mediating mechanisms. Moreover, there seems to be the possibility that in the frame of activation by bispecific antibodies T cells recognize tumor-specific antigens via their receptor, whereby a long-lasting immunization is initiated (FIG. 4B). Of particular importance in this respect is the intact Fc portion of the bispecific or trispecific antibody mediating the binding to accessory cells such as monocytes/macrophages and dendritic cells and causing them to develop cytotoxicity themselves and/or concomitantly transfer important co-stimulatory signals to the T cell. Obviously, in this manner a T cell response may be induced against tumor-specific peptides which have been unknown up to now.

By redirecting possibly anergized tumor-specific T cells to tumor cells by means of bispecific and/or trispecific antibodies and simultaneous co-stimulation of such T cells by accessory cells binding to the Fc portion of the bispecific or trispecific antibody the anergic state of cytotoxic T cells (CTLs) could be abolished. I.e., a preexisting T cell tolerance existing in the patient against the tumor may be abolished by means of intact heterologous bispecific and/or trispecific antibodies and, thus, a long-lasting anti-tumor immunity may be induced.

This last issue is supported by initial in vivo data from experiments with mice indicating the development of a long-lasting anti-tumor immunity of this type after treatment with a syngeneic tumor and intact bsabs. In these experiments, 14 out of 14 test animals which were successfully treated with bsabs following a first tumor injection survived a second tumor injection carried out 144 days after the first injection—without additional bsab administration.

Preferably, the antibodies employed according to the present invention are capable of reactivating tumor-specific antigens being in a state of anergy. Furthermore, they are capable of inducing tumor-reactive complement-binding antibodies and therefore to induce a humoral immune response.

Binding to the T cell preferably takes place via CD3, CD2, CD4, CD5, CD6, CD8, CD28, and/or CD44. The Fc receptor-positive cells have at least one Fcγ receptor I, II, or III.

Antibodies which may be employed according to the present invention are able to bind to monocytes, macrophages, dendritic cells, "natural killer" cells (NK cells) and/or activated neutrophils being Fcγ receptor I and/or II-positive cells.

The antibodies which may be employed according to the invention lead to the initiation or increase of the expression of CD40, CD80, CD86, ICAM-1, and/or LFA-3 being co-stimulatory antigens, or/and secretion of cytokines by the Fc receptor-positive cell. Preferably, the cytokines are IL-1, IL-2, IL-4, IL-6, IL-8, IL-12, INF-γ and/or TNF-α.

Preferably, binding to the T cell takes place via the T cell receptor complex of the T cell.

The bispecific antibodies which may be employed according to the present invention are for example:

an anti-CD3 X anti-tumor-associated antigen antibody and/or anti-CD4 X anti-tumor-associated antigen antibody and/or anti-CD5 X anti-tumor-associated antigen antibody and/or anti-CD6 X anti-tumor-associated antigen antibody and/or anti-CD8 X anti-tumor-associated antigen antibody and/or anti-CD2 X anti-tumor-associated antigen antibody and/or anti-CD28 X anti-tumor-associated antigen antibody and/or anti-CD44 X anti-tumor-associated antigen antibody.

The trispecific antibodies which may be employed according to the present invention preferably are:

an anti-CD3 X anti-tumor-associated antigen antibody and/or anti-CD4 X anti-tumor-associated antigen antibody and/or anti-CD5 X anti-tumor-associated antigen antibody and/or anti-CD6 X anti-tumor-associated antigen antibody and/or anti-CD8 X anti-tumor-associated antigen antibody and/or anti-CD2 X anti-tumor-associated antigen antibody and/or anti-CD28 X anti-tumor-associated antigen antibody and/or anti-CD44 X anti-tumor-associated antigen antibody.

The trispecific antibodies which may be used according to the present invention at least have one T cell binding arm, one tumor cell binding arm as well as an arm binding to Fc receptor-positive cells. This last binding arm may be an anti-Fc receptor binding arm or a mannose receptor binding arm.

Preferably, the bispecific antibody is a heterologous intact rat/mouse bispecific antibody.

By means of the bispecific and trispecific antibodies which may be used according to the present invention, T cells are activated and redirected against the tumor cells. Preferred useful heterologous intact bispecific antibodies are selected from one or more of the following combinations of isotypes:

rat-IgG2b/mouse-IgG2a,
rat-IgG2b/mouse-IgG2b,
rat-IgG2b/mouse-IgG3;
rat-IgG2b/human-IgG1, rat-IgG2b/human-IgG2,
rat-IgG2b/human-IgG3 [oriental allotype G3m(st) binding to protein A],
rat-IgG2b/human-IgG4;
rat-IgG2b/rat-IgG2c;
mouse-IgG2a/human-IgG3 [caucasian allotypes G3m (b+g)=no binding to protein A, in the following indicated as *]
mouse-IgG2a/mouse-[VH-CH1, VL-CL]-human-IgG1-[hinge]-human-IgG3*-[CH2-CH3]
mouse-IgG2a/rat-[VH-CH1, VL-CL]-human-IgG1-[hinge]-human-IgG3*-[CH2-CH3]
mouse-IgG2a/human-[VH-CH1, VL-CL]-human-IgG1-[hinge]-human-IgG3*-[CH2-CH3]
mouse-[VH-CH1, VL-CL]-human-IgG1/rat-[VH-CH1, VL-CL]-human-IgG1-[hinge]-human-IgG3*-[CH2-CH3]
mouse-[VH-CH1, VL-CL]-human-IgG4/rat-[VH-CH1, VL-CL]-human-IgG4-[hinge]-human-IgG4[N-terminal region of CH2]-human-IgG3*[C-terminal region of CH2: >aa position 251]-human-IgG3*[CH3]
rat-IgG2b/mouse-[VH-CH1, VL-CL]-human-IgG1-[hinge-CH2-CH3]
rat-IgG2b/mouse-[VH-CH1, VL-CL]-human-IgG2-[hinge-CH2-CH3]
rat-IgG2b/mouse-[VH-CH1, VL-CL]-human-IgG3-[hinge-CH2-CH3, oriental allotype]
rat-IgG2b/mouse-[VH-CH1, VL-CL]-human-IgG4-[hinge-CH2-CH3]
human-IgG1/human-[VH-CH1, VL-CL]-human-IgG1-[hinge]-human-IgG3*-[CH2-CH3]
human-IgG1/rat-[VH-CH1, VL-CL]-human-IgG1-[hinge]-human-IgG4[N-terminal region of CH2]-human-IgG3*[C-terminal region of CH2: >aa position 251]-human-IgG3*[CH3]
human-IgG1/mouse-[VH-CH1, VL-CL]-human-IgG1-[hinge]-human-IgG4[N-terminal region of CH2]-human-IgG3*[C-terminal region of CH2: >aa position 251]-human-IgG3*[CH3]
human-IgG1/rat-[VH-CH1, VL-CL]-human-IgG1-[hinge]-human-IgG2[N-terminal region of CH2]-human-IgG3*[C-terminal region of CH2: >aa position 251]-human-IgG3*[CH3]
human-IgG1/mouse-[VH-CH1, VL-CL]-human-IgG1-[hinge]-human-IgG2[N-terminal region of CH2]-human-IgG3*[C-terminal region of CH2: >aa position 251]-human-IgG3*[CH3]
human-IgG1/rat-[VH-CH1, VL-CL]-human-IgG1-[hinge]-human-IgG3*-[CH2-CH3]
human-IgG1/mouse-[VH-CH1, VL-CL]-human-IgG1-[hinge]-human-IgG3*-[CH2-CH3]
human-IgG2/human-[VH-CH1, VL-CL]-human-IgG2-[hinge]-human-IgG3*-[CH2-CH3]
human-IgG4/human-[VH-CH1, VL-CL]-human-IgG4-[hinge]-human-IgG3*-[CH2-CH3]
human-IgG4/human-[VH-CH1, VL-CL]-human-IgG4-[hinge]-human-IgG4[N-terminal region of CH2]-human-IgG3*[C-terminal region of CH2: >aa position 251]-human-IgG3*[CH3]
mouse-IgG2b/rat-[VH-CH1, VL-CL]-human-IgG1-[hinge]-human-IgG3*-[CH2-CH3]
mouse-IgG2b/human-[VH-CH1, VL-CL]-human-IgG1-[hinge]-human-IgG3*-[CH2-CH3]
mouse-IgG2b/mouse-[VH-CH1, VL-CL]-human-IgG1-[hinge]-human-IgG3*-[CH2-CH3]
mouse-[VH-CH1, VL-CL]-human-IgG4/rat-[VH-CH1, VL-CL]-human-IgG4-[hinge]-human-IgG4-[CH2]-human-IgG3*-[CH3]
human-IgG1/rat-[VH-CH1, VL-CL]-human-IgG1-[hinge]-human-IgG4-[CH2]-human-IgG3*-[CH3]
human-IgG1/mouse-[VH-CH1, VL-CL]-human-IgG1-[hinge]-human-IgG4-[CH2]-human-IgG3*-[CH3]
human-IgG4/human-[VH-CH1, VL-CL]-human-IgG4-[hinge]-human-IgG4-[CH2]-human-IgG3*-[CH3]

Preferably, the antibodies useful according to the present invention are monoclonal, chimeric, recombinant, synthetic, semi-synthetic, or chemically modified intact antibodies having for example Fv, Fab, scFv, or F(ab)$_2$ fragments.

Preferably, antibodies or derivatives or fragments thereof of human origin are used, or those modified to be suitable for the use in humans (so-called "humanized antibodies") (see for example Shalaby et al., J. Exp. Med. 175 (1992), 217; Mocikat et al., Transplantation 57 (1994), 405).

The preparation of the different types of antibodies and antibody fragments mentioned above is well-known to the skilled artisan. The preparation of monoclonal antibodies, preferably of mammalian origin, e.g. of human, rat, mouse, rabbit, or goat, can be performed using conventional methods as those described for example in Köhler and Milstein (Nature 256 (1975), 495), in Harlow and Lane (Antibodies, A Laboratory Manual (1988), Cold Spring Harbor) or in Galfré (Meth. Enzymol. 73 (1981), 3) or in DE 195 31 346.

It is further possible to prepare the antibodies described by means of recombinant DNA technology according to techniques known to the skilled artisan (see Kurucz et al., J. Immunol. 154 (1995), 4576; Hollinger et al., Proc. Natl. Acad. Sci. USA 90 (1993), 6444).

The preparation of antibodies having two different specificities, so-called bispecific antibodies, can be performed on the one hand using recombinant DNA technology but on the other hand also by the so-called hybrid hybridoma fusion technique (see for example Milstein et al., Nature 305 (1983), 537). This technique includes the fusion of hybridoma cell lines each producing antibodies with one of the desired specificities and identifying and isolating recombinant cell lines producing antibodies with both specificities.

The problem underlying the present invention can be solved using either having the following properties of: binding to a T cell; binding to at least one antigen on autologous tumor cells or allogeneic tumor cells; and binding via Fc portions (in the case of bispecific antibodies) or via a third specificity (in the case of trispecific antibodies) to Fc receptor-positive cells. To provide such bispecific and trispecific antibodies belongs to the prior art, and references describing such methods of preparation are incorporated herein by reference in their entirety.

The preparation of antibodies exhibiting three specificities, so-called trispecific antibodies, which are also suitable to solve the problem underlying the present invention may be for example carried out by coupling to one of the IgG heavy chains of a bispecific antibody a third antigen binding site having an additional specificity, e.g. in the form of "single chain variable fragments" (scFv). The scFv may be coupled for example using a -S-S($G_4S$)$_n$D-I-linker (SEQ ID NO:1)

to one of the heavy chains (S=serine, G=glycine, D=aspartate, I=isoleucine).

Figure 5:
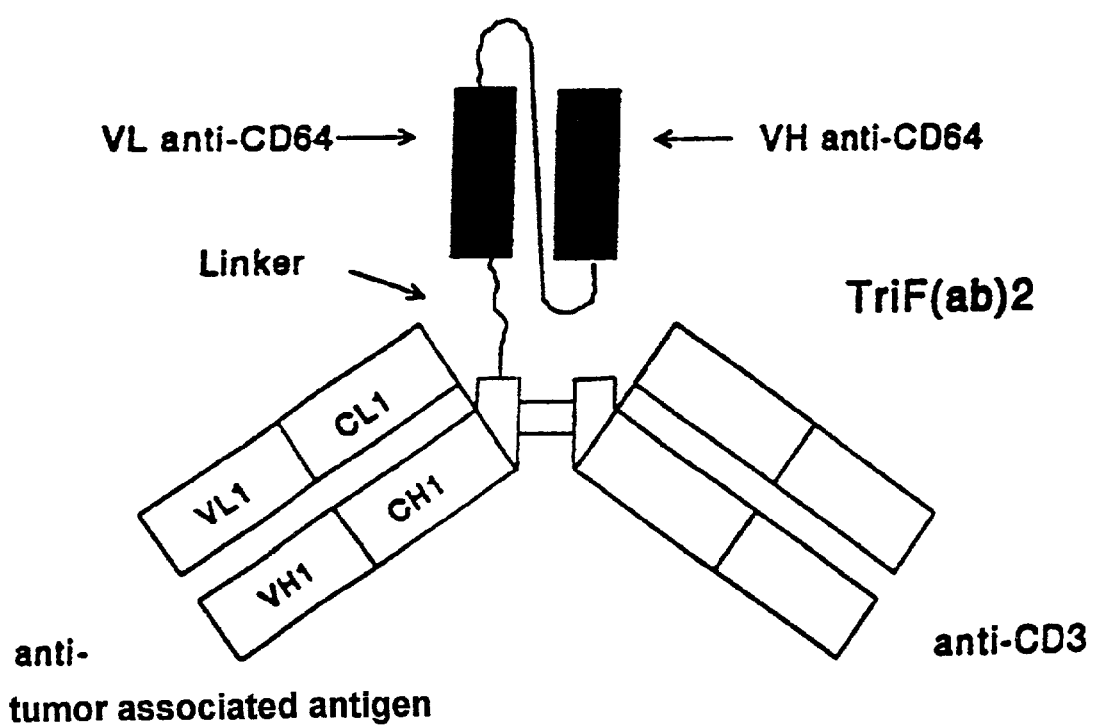

Analogously, trispecific F(ab)$_2$ constructs may be prepared by replacing the CH2-CH3 regions of the heavy chain of one specificity of a bispecific antibody by an scFv having a third specificity, while the CH2-CH3 regions of the heavy chain having the other specificity can be removed for example by insertion of a stop codon (at the end of the "hinge" region) into the coding gene, e.g. by homologous recombination (see FIG. 5).

Figure 6:
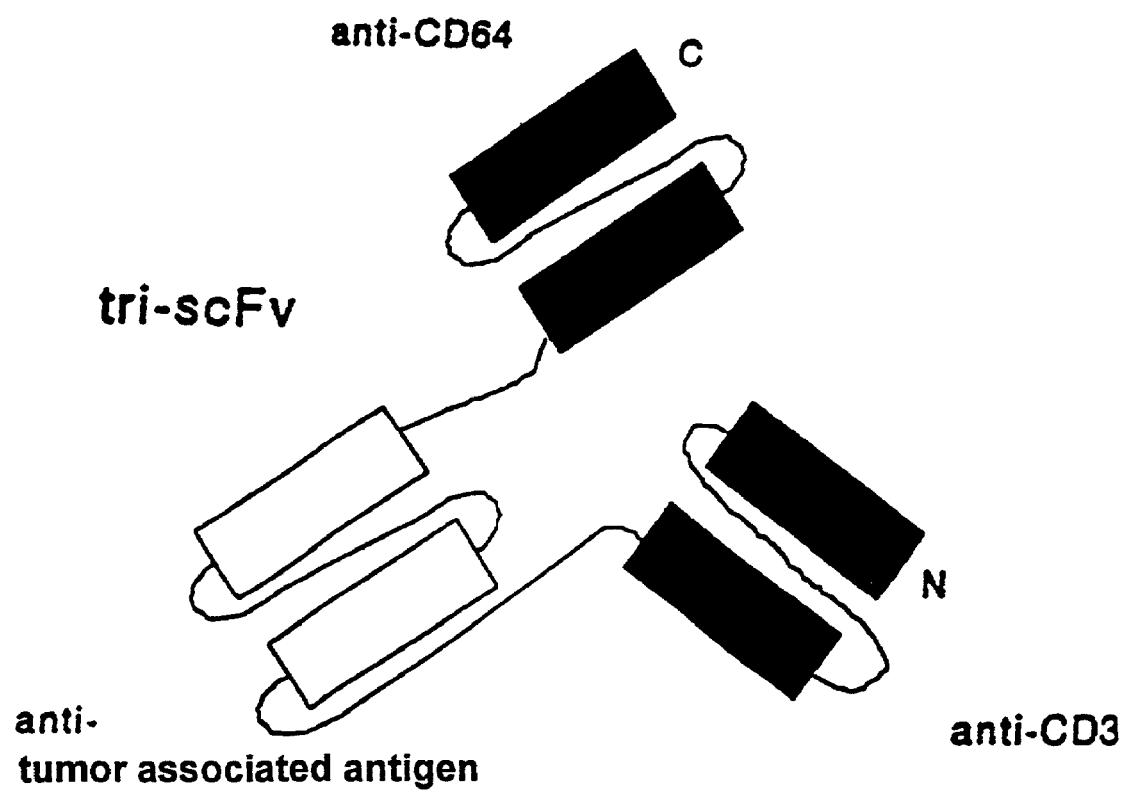

It is also possible to prepare trispecific scFv constructs wherein three VH-VL regions representing three different specificities are arranged in series (FIG. 6).

According to the present invention there are for example used intact bispecific antibodies. Intact bispecific antibodies are composed of two antibody semi-molecules (each having a H and a L immunoglobulin chain) each representing a specificity, and additionally having a Fc portion like normal antibodies which performs the well-known effector functions. They are preferably prepared using the quadroma technology. This method of preparation is exemplified in DE-A-44 19 399. For complete disclosure this document is incorporated by reference in its entirety also with respect to a definition of bispecific antibodies. It should be understood that also other methods of preparation are useful if they lead to the intact bispecific antibodies according to the above definition which are required according to the present invention.

For example, intact bispecific antibodies may be produced in sufficient amounts using a newly developed method of preparation (6). The combination of 2 bispecific antibodies directed against 2 different tumor-associated antigens (e.g. c-erb-B2, ep-cam, such as GA-733-2=C215) on the mammary carcinoma cells minimizes the risk that tumor cells expressing only one of the antigens would not be recognized.

It has also been attempted to achieve an anti-tumor-immunity by treatment with bispecific F(ab')2 fragments having the specificities anti-c-erb-B2 x anti-CD64. The main disadvantage of bsF(ab')2 fragments is that due to the specificities used only FcγRI+ cells may be redirected to the tumor. By this bispecific antibody T cells are not redirected to the tumor. Although FcγRI+ cells may activate tumor-specific T cells indirectly by presentation of tumor-specific peptides (via MHC I or MHC II, respectively) following e.g. phagocytosis of tumor cell components, the efficiency of the induction of an anti-tumor immunity in this case is lower since T cells are not bound by this bsab and may also not contribute to co-stimulation of the Fc receptor-positive cells.

Further advantages of intact bsabs able to redirect T cells as compared to the above-mentioned bsF(ab')2 fragments may be detailed as follows:

1. It is possible for Fc receptor-positive cells to bind to intact bsabs and to contribute on the one hand directly to tumor killing via ADCC (antibody-dependent cell-mediated cytotoxicity) and on the other hand to T cell activation as detailed above.

2. Intact T cell-redirecting bsabs function also in targeting anergized tumor-specific T cells to the tumor cell which according to the invention may be reactivated directly at the tumor site. This may not be achieved by an bsF(ab')2 fragment having the specificities of anti-CD64 X anti-tumor-associated antigen.

3. A bsF(ab')2 fragment having the specificities of anti-CD64 X anti-tumor-associated antigen is only able to achieve an anti-tumor immunity in 30% of the patients while according to the present invention using T cell-redirecting intact bsabs in experiments with mice a protection of 100% of the animals could be achieved.

The binding of the bsab to Fcγ-RI shows two essential advantages with regard to an optimal anti-tumor effectiveness:

(1) Fcγ-RI-positive cells have the ability to eliminate tumor cells by ADCC and, thus, are able to contribute synergistically to the anti-tumor effect of the cytotoxic T cells directed to the tumor cell by the bsabs.

(2) FcγRI-positive cells (such as monocytes/macrophages/dendritic cells) are able to provide important co-stimulatory signals similar to antigen presentation to the T cell and, thereby, prevent anergizing of the T cell. Furthermore, as shown in FIG. 4, even T cells having a T cell receptor which recognizes tumor-specific peptides (presented via MHC antigens on the tumor cell) can be stimulated as a desired by-product due to the bsab-mediated interaction of the T cell with accessory cell and tumor cell. In this constellation, the co-stimuli necessary for correct activation of the T cell would be provided by the accessory cell (such as the monocyte). Thus, besides the direct T cell receptor-independent bsab-mediated tumor destruction (FIG. 4A) the antibody of the present invention should also be able to activate and generate tumor-specific T cells (FIG. 4B) which after degradation of the bsab continue to patrol in the patient. This means, that similar to gene-therapeutical approaches (e.g. by incorporation of co-stimulatory antigens such as B-7 into the tumor cell) the tumor tolerance in the patient may be abolished by means of intact bsabs.

In this respect it is further advantageous that the expression of Fcγ-RI on the respective cells is up-regulated after G-CSF treatment.

In another preferred embodiment of the present invention, the intact, preferably heterologous specific and/or trispecific antibodies used according to the present invention have the following properties:

a) binding to a T cell;
b) binding to at least one antigen on a target cell;
c) binding, via their Fc portion (in the case of bispecific antibodies) or a third specificity (in the case of trispecific antibodies), to Fc receptor-positive cells whereby they induce an immune response and/or destroy target cells wherein the antibody is selected to bind to a surface antigen as the target antigen on the target cell which may be induced and which is not present on the target cell in the uninduced state (normal state) or is present in an amount which is so low that the number is insufficient for destruction of the target cell (FIGS. 7A and 7B).

It has been shown that following induction already a relatively small number of target antigens on the target cell is sufficient to bind the intact bispecific and trispecific antibodies and to induce destruction of the target cell and/or an immune response. According to the invention, "small number" represents a number of target antigens on the target cell of more than 100 target antigens per target cell, preferably more than 300 and further preferred more than 1000 target antigens per target cell. The inducible target antigens may also be present in an amount of up to 500,000 per target cell, wherein also amounts up to 400,000, up to 300,000, up to 200,000 or up to 100,000 per target cell are inducible. A further preferred range of the amount in which the target antigens may be present is from 50,000 to 100,000 and from 5000 to 50,000.

Examples of inducible surface antigens on target cells (target antigens) which may be used for an immunotherapy by intact bispecific and trispecific antibodies are heatshock proteins and "MHC class I-related" MIC molecules. Heat shock proteins (Hsp) are synthesized by the cell in response of cellular stress. According to the present invention, "cellular stress" for example includes a degeneration of the cell, the effect of radiation, chemical substances and of elevated temperature on the cell as well as an infection of the cell by microorganisms. At present, four families of heat shock proteins are known which are distinguished by differences in molecular weight. These families are referred to as Hsp25, Hsp60, Hsp70, and Hsp90 wherein the number gives the approximate molecular weight of the stress proteins in kilodaltons. The heat shock proteins are characterized by highly conserved amino acid sequences where the degree of conservation is more than 35% of amino acid identity, preferably 35–55%, further preferred 55–65% and most preferred between 75% to 85% amino acid identity.

Reference is made to the following review articles: Annu. Rev. Genet. 27, 437–496 (1993); Biochimie 76, 737–747 (1994); Cell. Mol. Life Sci. 53, 80–129, 168–211 (1997); Experientia 48, 621–656 (1992); Kabakov & Gabai, Heat Shock Proteins and Cytoprotection, Berlin: Springer 1997.

Normally, heat shock proteins are not expressed in healthy tissue. However, there are studies which show that heat shock proteins may for example be expressed on tumor cell lines and tumor material from patients (Melcher et al., Nature Medicine, 4: 581, 1998). However, the expression of the heat shock proteins on the tumor cell lines is relatively weak and therefore unsuitable for immunotherapeutical approaches known up to now using monoclonal antibodies and incomplete (F(ab)2) bispecific antibodies.

Examples of heat shock proteins are Hsp60 and Hsp70/72.

The same applies to MIC molecules. Also these molecules may be induced by cellular stress as defined in more detail above. MIC molecules are MHC I-related molecules being under the control of heat shock promoter elements (Groh et al. PNAS 93: 12445, 1996). Examples of MIC molecules are MIC A and MIC B. It could be demonstrated also for MIC molecules that on normal tissue they are not expressed or expressed in such a low amount that they are unsuitable as a target structure for the recognition by an antibody to achieve the destruction of the cell, while for example on epithelial tumors they are expressed in such a high amount that they may be used as target antigens in an immunotherapy by the bispecific and trispecific antibodies provided by the present invention.

The intact bispecific or trispecific antibodies provided according to the present invention are selected to be directed against at least one target antigen on a target cell which is inducible and is not present or essentially not present on the target cell in the uninduced state. This number for example is about 100 target antigens/cell. However, this does not mean that such target antigen are absent from other cells, i.e. non-target cells. For example, heat shock proteins are present on quickly regenerating tissue, e.g. the mucous cells of the gastro-intestinal tract also in the physiological state when they are constitutively expressed. However, these heat shock proteins are not included in the present invention since they are not inducible but are present already on normal tissue. By the antibodies of the present invention directed against heat shock proteins, also certain mucous cells of the gastro-intestinal tract may be destroyed since these, as explained above, constitutively express heat shock proteins on their surfaces. Although the possible destruction of said cells is a disadvantage for the patient, this is considered to be negligible as compared to tumor destruction which may be achieved.

Thus, quickly regenerating tissue is not the primary target for the antibodies according to the present invention, but may be "hit" by the antibodies if the antibody according to the present invention not only recognizes the inducible target antigens on the target cell but these antigens are present e.g. also on quickly regenerating tissue. However, since these tissues divide quickly, after termination of the antibody therapy the original state of this tissue may be quickly regenerated so that it may again fulfill its physiological function. Therefore, the invention does not relate to the recognition by the bispecific and trispecific antibodies according to the present invention of antigens on e.g. quickly regenerating tissue where they may possibly be constitutively expressed but the invention exclusively comprises those antibodies directed against target antigens which are inducible in the target cell and may be expressed, for example constitutively expressed, after induction.

According to the present invention, "inducible" refers to those target antigens which are operationally tumor-specific herein and are not present on the cell in its physiological state or present in such a small number that no immune response could be induced against said antigens or due to this small number a destruction of the target cells does not occur or only occurs to an extent which is not substantial or therapeutically useful.

The term "inducible target antigens on a target cell" is not intended to refer only to those on a tumor cell but also to antigens which are induced upon infection of the target cell e.g. by a microorganism. According to the present invention, "microorganism" is meant to be any organism affecting the target cell in a way that on its surface a target antigen induced by the microorganism is expressed to the extent described above. According to the invention, microorganisms are meant to be for example bacteria, viruses, protozoa and fungi. Bacteria include for example Gram-positive and Gram-negative bacteria, mycoplasmas and rikettsia. The protozoa particularly comprise plasmodia. Viruses particularly comprise retroviruses, adenoviruses, herpes viruses, hepatitis viruses, togaviruses, pox viruses etc. It is important that in cells infected by one or more of said microorganisms antigens are expressed on the cell surface which are induced by the microorganism infection. This refers to antigens produced by the target cells in response to the microorganism infection and appear on the cell surface (host antigens) and not to target antigens produced by the microorganisms themselves. Infection of a target cell by a microorganism also results in a cellular stress situation for the cell which in response induces the expression of certain proteins, such as heat shock proteins and MIC proteins.

The intact bispecific and trispecific antibodies provided by the present invention serve to target not only one type of immune cells to the target cell but to target also T cells and accessory cells and therefore are particularly suitable for the recognition of inducible surface antigens being the operational target structures. It could be demonstrated that already a small number of target antigens in an amount of 100 to 5000 per cell on the target cell are sufficient to achieve its destruction. The in vitro experiments performed for this purpose using stem cell preparations (PBSZ) are described in Example 2. Thus, the class of intact bispecific and trispecific antibodies according to the present invention is capable of destroying tumor cells or target cells or to initiate an immune response after recognition of these cells even if the expression of the target antigens is very low.

Since they are directed against inducible antigens, the antibodies according to the present invention may contribute to solving the problem of a lack of target cell-specific target antigens required for an immunotherapy on tumor cells and on cells infected by microorganisms. Because such inducible antigens are present not only on tumor cells but are generally produced in stress situations it is also possible to treat by means of immunotherapy diseases caused by infection with for example viruses, single-celled organisms or fungi. These include the MIC molecules and heat shock proteins already detailed above.

EXAMPLE 2

After evidence had been obtained for the extraordinary effectivity of intact bsabs in preclinical animal models not only in vitro but also in vivo (Lindhofer et al., Blood, 88: 4651, 1996) the purification of stem cell preparations from contaminating tumor cells was developed as another possibility of use (Lindhofer et al., Exp. Hematol. 25: 879, 1997).

Based upon these experiments subsequent experiments with complete stem cell preparations (about $2 \times 10^{10}$ cells) were able to demonstrate particularly an effectivity in the subsaturated range of target antigens. I.e. in titration experiments the amount of bsab administered was so low that in a PBSZ (peripheral blood stem cell) preparation containing approximately $6.5 \times 10^9$ T cells at a dose of 5 µg of antibody/preparation only 3000 CD3 molecules of about 30,000 CD3 molecules/T cell were bound by the bsab (see calculation). Still, the intact bsabs were capable of destroying the target cells (here tumor cell HCT-8) also under these conditions.

The experiments were performed in a way that aliquots were taken from the thus treated PBSZ preparations and contaminated with a defined amount of tumor cells. It could be demonstrated that the tumor cells are destroyed even at this low concentration of intact bsabs at which only a portion of the target antigens is occupied.

The evaluation of the above-described experiment gave the following results:

| Patient WaGr total cell number PBSZ: $2.5 \times 10^{10}$ + 5 µg of bsab | | | |
|---|---|---|---|
| Aliquot Plate | $5 \times 10^6$ PBSZ + no antibody | bsab + bsab anti-CD3 x epcam | Tumor cells Tumor cells/ mononucleated cells (PBSZ)/well |
| 24 | 6/6* | 0/6° | $2 \times 10^4/2 \times 10^6$ |
| 96 | 12/12 | 0/12 | $5000/5 \times 10^5$ |
| tumor reduction: | none | <5 log | Tumor ratio: 1% $°\Sigma = 1.2 \times 10^5$ Tumor cells/ 6 wells |

*Number of wells showing tumor growth of 6 or 12 plates wells, respectively, after 14 days of culture.
°Titration experiments using HCT-8 tumor cell line showed that already 1–2 tumor cells/well are sufficient to represent a clear tumor growth which may be visually evaluated after 14 days of culture.

Calculation:

An intact bsab has a molecular weight of 150 kDa, i.e. 1 mole correspond to 150 kg and according to definition correspond to $6 \times 10^{23}$ molecules. Thus, 5 µg correspond to approx. $2 \times 10^{13}$ molecules.

Since $6.5 \times 10^9$ T cells were determined in a stem cell preparation and one T cell approximately carries 30,000 CD3 molecules, a total number of $19.5 \times 10^{13}$ CD3 molecules is calculated for the stem cell preparation.

Since each of the bsabs has one anti-CD3 binding arm it may be concluded that, theoretically, comparing the two numbers of molecules calculated above in this particular example not more than about 3000 CD3 molecules may be occupied by the bsabs.

REFERENCES

1. Haagen et al., Interaction of human monocyte Fcγ receptors with rat IgG2b, *J. Immunology.*, 1995, 154: 1852–1860
2. Gast G. C., Haagen I.-A., van Houten A. A., Klein S., Duits A. J., de Weger R. A., Vroom T. M., Clark M. R., J. Phillips, van Dijk A. J. G., de Lau W. B. M., Bast B. J. E. G. CD8 T-cell activation after intravenous administration of CD3 x CD19 bispecific antibody in patients with non-Hodgkin lymphoma. Cancer Immunol. Immunother. 40: 390, 1995
3. Tenny, C., Jacobs, S., Stoller, R., Earle, M., and Kirkwood, J. Adoptive cellular immunotherapy with high-dose chemotherapy and autologous bone marrow rescue (ABMR) for recurrent breast cancer (meeting abstr.). Proc. Annu. Meet. Am. Soc. Clin. Oncol. 11: A88, 1992 ISSN: 0736-7589. CO: PHAODO-7589 CO, 1993.
4. Early Breast Cancer Trialists' Collaborative Group, Systemic treatment of early breast cancer by hormonal, cytotoxic, or immune therapy—133 randomized trials involving 31 000 recurrences and 24 000 deaths among 75 000 women. Part II *Lancet* 339:71–85, 1992
5. Guo et al., Effective tumor vaccines generated by in vitro modification of tumor cells with cytokines and bispecific monoclonal antibodies. Nature Medicine 3: 451, 1997
8. Lindhofer et al, Preferential species-restricted heavy-light chain pairing in rat-mouse quadromas: Implications for a single step purification of bispecific antibodies, *J. Immunology* 1995, 155:219

What is claimed is:

1. A method for inducing immunity against a tumor in a patient, comprising administering to the patient in a time-staggered manner: (1) autologous tumor cells or allogeneic tumor cells of the same tumor type each treated to prevent their survival after reinfusion; and (2) intact bispecific and/or trispecific antibodies having the following properties of:
 (a) binding to a T cell;
 (b) binding to at least one antigen on said autologous tumor cell or said allogeneic tumor cell; and
 (c) binding via their Fc portion (in the case of bispecific antibodies) or via a third specificity (in the case of trispecific antibodies) to Fc receptor-positive cells,
wherein there is a time interval of 1–48 hours between the administration of (1) and the administration of (2).

2. The method according to claim 1 wherein the administration of said tumor cells is prior to or after the administration of said antibodies.

3. The method according to claim 1 wherein the interval is 1–24 hours.

4. The method of claim 3, wherein the interval is 1–12 hours.

5. The method of claim 4, wherein the interval is 1–6 hours.

6. The method of claim 5, wherein the interval is 1–4 hours.

7. The method of claim 6, wherein the interval is 2–4 hours.

8. The method according to claim 1 wherein the antibodies are administered in an amount of about 5–500 µg in each infusion.

9. The method of claim 8, wherein the antibodies are administered in an amount of about 10–300 µg.

10. The method of claim 9, wherein the antibodies are administered in an amount of about 10–100 µg.

11. The method of claim 10, wherein the antibodies are administered in an amount of about 10–50 µg.

12. The method of claim 8, wherein the tumor cells are administered in an amount of about $10^7$–$10^9$ cells.

13. The method of claim 12, wherein the tumor cells are administered in an amount of about $10^8$ cells.

14. The method according to claim 1 wherein said Fc receptor-positive cells have an Fcγ receptor I, II, or III.

15. The method according to claim 14 wherein said antibodies are able to bind to monocytes, makrophages, dendritic cells, "natural killer" cells (NK cells) and/or activated neutrophils being Fcγ receptor I-positive cells.

16. The method according to claim 1 wherein said antibodies are capable of inducing tumor-reactive complement-binding antibodies and therefore of inducing a humoral immune response.

17. The method according to claim 1 wherein said antibodies are selected to bind to the T cells via CD2, CD3, CD4, CD5, CD6, CD8, CD28, and/or CD44.

18. The method according to claim 1 wherein said antibodies are selected so that following their binding to the Fc receptor-positive cells the expression of CD40, CD80, CD86, ICAM-1, and/or LFA-3 being co-stimulatory antigens and/or the secretion of cytokines by the Fc receptor-positive cell is initiated or increased.

19. The method according to claim 18 wherein the antibodies are selected so that the secretion of IL-1, IL-2, IL-4, IL-6, IL-8, IL-12, INF-γ being cytokines and/or of TNF-α is increased.

20. The method according to claim 1 wherein said bispecific antibody is selected from the group consisting of an anti-CD3 X anti-tumor-associated antigen antibody, anti-CD4 X anti-tumor-associated antigen antibody, anti-CD5 X anti-tumor-associated antigen antibody, anti-CD6 X anti-tumor-associated antigen antibody, anti-CD8 X anti-tumor-associated antigen antibody, anti-CD2 X anti-tumor-associated antigen antibody, anti-CD28 X anti-tumor-associated antigen antibody, and anti-CD44 X anti-tumor-associated antigen antibody.

21. The method according to claim 1 wherein said bispecific antibody is selected from one or more of the following combinations of isotypes:
 rat-IgG2b/mouse-IgG2a,
 rat-IgG2b/mouse-IgG2b,
 rat-IgG2b/mouse-IgG3,
 rat-IgG2b/human-IgG1,
 rat-IgG2b/human-IgG2,
 rat-IgG2b/human-IgG3[oriental allotype G3m(st)=binding to protein A],
 rat-IgG2b/human-IgG4,
 rat-IgG2b/rat-IgG2c,
 mouse-IgG2a/human-IgG3[caucasian allotypes G3m (b+g)=no binding to protein A, in the following indicated as *]
 mouse-IgG2a/mouse-[VH-CH1, VL-CL]-human-IgG1-[hinge]-human-IgG3*-[CH2-CH3]
 mouse-IgG2a/rat-[VH-CH1, VL-CL]-human-IgG1-[hinge]-human-IgG3*-[CH2-CH3]
 mouse-IgG2a/human-[VH-CH1, VL-CL]-human-IgG1-[hinge]-human-IgG3*-[CH2-CH3]
 mouse-[VH-CH1, VL-CL]-human-IgG1/rat-[VH-CH1, VL-CL]-human-IgG1-[hinge]-human-IgG3*-[CH2-CH3]
 mouse-[VH-CH1, VL-CL]-human-IgG4/rat-[VH-CH1, VL-CL]-human-IgG4-[hinge]-human-IgG4[N-terminal region of CH2]-human-IgG3*[C-terminal region of CH2: >aa position 251]-human-IgG3*[CH3]
 rat-IgG2b/mouse-[VH-CH1, VL-CL]-human-IgG1-[hinge-CH2-CH3]
 rat-IgG2b/mouse-[VH-CH1, VL-CL]-human-IgG2-[hinge-CH2-CH3]
 rat-IgG2b/mouse-[VH-CH1, VL-CL]-human-IgG3-[hinge-CH2-CH3, oriental allotype]
 rat-IgG2b/mouse-[VH-CH1, VL-CL]-human-IgG4-[hinge-CH2-CH3]
 human-IgG1/human-[VH-CH1, VL-CL]-human-IgG1-[hinge]-human-IgG3*-[CH2-CH3]

human-IgG1/rat-[VH-CH1, VL-CL]-human-IgG1-[hinge]-human-IgG4 [N-terminal region of CH2]-human-IgG3*[C-terminal region of CH2: >aa position 251]-human-IgG3*[CH3]
human-IgG1/mouse-[VH-CH1, VL-CL]-human-IgG1-[hinge]-human-IgG4[N-terminal region of CH2]-human-IgG3*[C-terminal region of CH2: >aa position 251]-human-IgG3*[CH3]
human-IgG1/rat-[VH-CH1, VL-CL]-human-IgG1-[hinge]-human-IgG2 [N-terminal region of CH2]-human-IgG3*[C-terminal region of CH2: >aa position 251]-human-IgG3*[CH3]
human-IgG 1/mouse-[VH-CH1, VL-CL]-human-IgG1-[hinge]-human-IgG2 [N-terminal region of CH2]-human-IgG3*[C-terminal region of CH2: >aa position 251]-human-IgG3*[CH3]
human-IgG1/rat-[VH-CH1, VL-CL]-human-IgG1-[hinge]-human-IgG3*-[CH2-CH3]
human-IgG1/mouse-[VH-CH1, VL-CL]-human-IgG1-[hinge]-human-IgG3*-[CH2-CH3]
human-IgG2/human-[VH-CH1, VL-CL]-human-IgG2-[hinge]-human-IgG3*-[CH2-CH3]
human-IgG4/human-[VH-CH1, VL-CL]-human-IgG4-[hinge]-human-IgG3*-[CH2-CH3]
human-IgG4/human-[VH-CH1, VL-CL]-human-IgG4-[hinge]-human-IgG4[N-terminal region of CH2]-human-IgG3*[C-terminal region of CH2: >aa position 251]-human-IgG3*[CH3]
mouse-IgG2b/rat-[VH-CH1, VL-CL]-human-IgG1-[hinge]-human-IgG3*-[CH2-CH3]
mouse-IgG2b/human-[VH-CH1, VL-CL]-human-IgG1-[hinge]-human-IgG3*-[CH2-CH3]
mouse-IgG2b/mouse-[VH-CH1, VL-CL]-human-IgG1-[hinge]-human-IgG3*-[CH2-CH3]
mouse-[VH-CH1, VL-CL]-human-IgG4/rat-[VH-CH1, VL-CL]-human-IgG4-[hinge]-human-IgG4-[CH2]-human-IgG3*-[CH3]
human-IgG1/rat-[VH-CH1, VL-CL]-human-IgG1-[hinge]-human-IgG4-[CH2]-human-IgG3*-[CH3]
human-IgG1/mouse-[VH-CH1, VL-CL]-human-IgG1-[hinge]-human-IgG4-[CH2]-human-IgG3*-[CH3]
human-IgG4/human-[VH-CH1, VL-CL]-human-IgG4-[hinge]-human-IgG4-[CH2]-human-IgG3*-[CH3].

22. The method according to claim 1 wherein said antibody is a heterologous bispecific or trispecific antibody.

23. The method of claim 22, wherein the heterologous bispecific antibody is a heterologous rat/mouse bispecific antibody.

24. The method according to claim 1 wherein the trispecific antibody comprises a T cell binding arm, a tumor cell binding arm and a third specificity for binding to Fc receptor-positive cells.

25. The method according to claim 24 wherein said trispecific antibody is selected from the group consisting of an anti-CD3 X anti-tumor-associated antigen antibody, anti-CD4 X anti-tumor-associated antigen antibody, anti-CD5 X anti-tumor-associated antigen antibody, anti-CD6 X anti-tumor-associated antigen antibody, anti-CD8 X anti-tumor-associated antigen antibody, anti-CD2 X anti-tumor-associated antigen antibody, anti-CD28 X anti-tumor-associated antigen antibody, and anti-CD44 X anti-tumor-associated antigen antibody.

26. The method according to claim 1 wherein tumor cells have been treated by irradiation or by a chemical substance.

27. The method of claim 26, wherein the irradiation is gamma irradiation.

28. The method of claim 26, wherein the irradiation has a dose of about 50 to 200 Gy.

29. The method of claim 26, wherein the chemical substance is mitomycin C.

30. The method according to claim 1 wherein said antibody binds to a surface antigen on said tumor cells, wherein said surface antigen is absent from non-tumor cells or is present in an amount insufficient for destruction of said non-tumor cells by the antibody.

31. The method according to claim 30 wherein the tumor cells are subjected to a heat pretreatment to increase the immunogenicity.

32. The method according to claim 30 wherein the surface antigen is heat shock proteins or MHC class I-related MIC molecules.

33. The method according to claim 32 wherein the heat shock proteins are HSP25, Hsp60 or Hsp70 (Hsp72) or Hsp90 proteins and the MIC molecules are MIC A or MIC B molecules.

34. The method according to claim 33 wherein the surface antigens are present in an amount of at least 100 and at the most 500,000 per tumor cell.

35. The method according to claim 34 wherein the antibody is capable of activating Fc receptor-positive cells whereby the expression of cytokines and/or co-stimulatory antigens is initiated or increased.

36. The method according to claim 1 wherein the time-staggered application of the intact bispecific and/or trispecific antibodies is performed several times.

37. The method of claim 1, wherein the tumor cells are administered in an amount of about $2 \times 10^4$ cells.

38. The method of claim 1, wherein the tumor cells are administered in an amount of about 5,000 cells.

39. The method of claim 1, wherein the antibodies are administered in an amount of about 1–100 µg.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:single chain
      variable fragment (scFv) coupling linker
<220> FEATURE:
<221> NAME/KEY: MOD_RES
<222> LOCATION: (3)..(7)
<223> OTHER INFORMATION: positions 3-7 (G-4S) may be repeated an
      unspecified number of times
```

```
<400> SEQUENCE: 1

Ser Ser Gly Gly Gly Gly Ser Asp Ile
 1               5
```